United States Patent
Dennis-Smither et al.

(10) Patent No.: US 11,427,524 B2
(45) Date of Patent: Aug. 30, 2022

(54) PROCESS FOR DEHYDRATING METHANOL TO DIMETHYL ETHER PRODUCT

(71) Applicants: BP P.L.C., London (GB); BP (CHINA) HOLDINGS LTD, Shanghai (CN)

(72) Inventors: Benjamin James Dennis-Smither, Hull (GB); John Glenn Sunley, Hull (GB)

(73) Assignee: BP P.L.C., London (GB)

( * ) Notice: Subject to any disclaimer, the term of this patent is extended or adjusted under 35 U.S.C. 154(b) by 133 days.

(21) Appl. No.: 16/641,629

(22) PCT Filed: Aug. 24, 2018

(86) PCT No.: PCT/CN2018/102072
§ 371 (c)(1),
(2) Date: Feb. 24, 2020

(87) PCT Pub. No.: WO2019/037766
PCT Pub. Date: Feb. 28, 2019

(65) Prior Publication Data
US 2021/0163389 A1    Jun. 3, 2021

(30) Foreign Application Priority Data

Aug. 24, 2017 (WO) ................ PCT/CN2017/098861

(51) Int. Cl.
*C07C 41/09* (2006.01)
*B01J 29/08* (2006.01)
(Continued)

(52) U.S. Cl.
CPC ............ *C07C 41/09* (2013.01); *B01J 29/084* (2013.01); *B01J 29/18* (2013.01); *B01J 29/40* (2013.01);
(Continued)

(58) Field of Classification Search
None
See application file for complete search history.

(56) References Cited

U.S. PATENT DOCUMENTS 4,560,807 A   12/1985  Murai et al.
8,450,521 B2   5/2013  Ditzel
(Continued)

FOREIGN PATENT DOCUMENTS

CN   1810752   8/2006
CN   1820849   8/2006
(Continued)

OTHER PUBLICATIONS

Foster, M.D., et al., Microporous and Mesoporous Materials, vol. 90, pp. 32-38, 2006.
(Continued)

*Primary Examiner* — Sheng H Davis
*Assistant Examiner* — Keling Zhang
(74) *Attorney, Agent, or Firm* — McDonnell Boehnen Hulbert & Berghoff LLP

(57) ABSTRACT

A process for dehydrating methanol to dimethyl ether product in the presence of a solid Brønsted acid catalyst which is an aluminosilicate zeolite or a heteropolyacid and a promoter which is (i) a ketone of formula $R^1COR^2$ (Formula I) in which $R^1$ and $R^2$ are identical or different and are each a $C_1$-$C_{11}$ alkyl group and furthermore $R^1$ and $R^2$ together with the carbonyl carbon atom to which they are bonded may form a cyclic ketone; or (ii) a ketal derivative of a ketone of Formula I; and the molar ratio of promoter to methanol is maintained at 0.5 or less.

17 Claims, 1 Drawing Sheet

(51) Int. Cl.
*B01J 29/18* (2006.01)
*B01J 29/40* (2006.01)
*B01J 29/65* (2006.01)
*B01J 29/70* (2006.01)
*B01J 31/02* (2006.01)
*B01J 31/26* (2006.01)
*C07C 43/04* (2006.01)

(52) U.S. Cl.
CPC ............... *B01J 29/65* (2013.01); *B01J 29/70* (2013.01); *B01J 29/7007* (2013.01); *B01J 29/7038* (2013.01); *B01J 29/7042* (2013.01); *B01J 31/0207* (2013.01); *B01J 31/26* (2013.01); *C07C 43/043* (2013.01); *B01J 2231/4288* (2013.01); *B01J 2531/007* (2013.01)

(56) References Cited

U.S. PATENT DOCUMENTS

| | | |
|---|---|---|
| 2012/0220804 A1 | 8/2012 | Mitschke et al. |
| 2017/0081267 A1 | 3/2017 | Daniel et al. |
| 2017/0096382 A1 | 4/2017 | Beckers et al. |

FOREIGN PATENT DOCUMENTS

| | | |
|---|---|---|
| CN | 101486629 | 7/2009 |
| CN | 101600678 A | 12/2009 |
| CN | 102215959 A | 10/2011 |
| CN | 104341279 | 2/2015 |
| CN | 105669452 | 6/2016 |
| CN | 104588060 B | 1/2017 |
| EP | 1396483 | 10/2004 |
| WO | 2004074228 | 9/2004 |
| WO | 2008073096 A1 | 6/2008 |
| WO | 2011027105 | 3/2011 |
| WO | 2013124404 | 8/2013 |
| WO | 2013124423 | 8/2013 |
| WO | 2014096254 | 6/2014 |
| WO | 2014125038 | 8/2014 |
| WO | 2015121411 | 8/2015 |
| WO | 2015193179 | 12/2015 |
| WO | 2015193182 | 12/2015 |
| WO | 2015193183 | 12/2015 |
| WO | 2015193185 | 12/2015 |
| WO | 2015193186 | 12/2015 |
| WO | 2015193188 | 12/2015 |

OTHER PUBLICATIONS

The International Search Report with Written Opinion for PCT/CN2018/102072 dated Oct. 26, 20187, p. 1-11.
The International Search Report with Written Opinion for PCT/CN2017/098861 dated May 23, 2018, p. 1-11.
The International Search Report with Written Opinion for PCT/CN2018/102137 dated Nov. 28, 2018, p. 1-9.
The International Search Report with Written Opinion for PCT/CN2017/098885 dated May 30, 2018, p. 1-10.
The International Search Report with Written Opinion for PCT/CN2018/102057 dated Nov. 9, 2018, p. 1-11.
The International Search Report with Written Opinion for PCT/CN2017/098839 dated May 22, 2018, p. 1-11.
The International Search Report with Written Opinion for PCT/CN2018/101954 dated Nov. 19, 2018, p. 1-11.
The International Search Report with Written Opinion for PCT/CN2017/098892 dated May 22, 2018, p. 10.

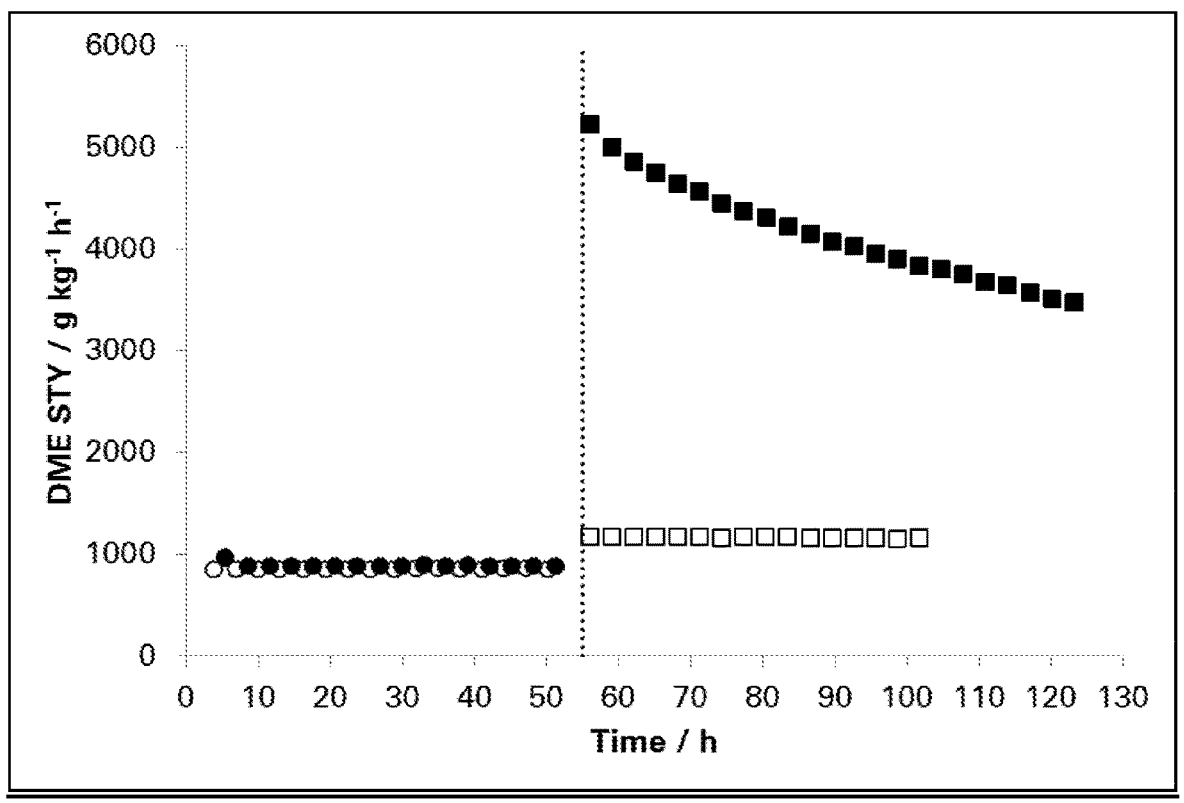

PROCESS FOR DEHYDRATING METHANOL TO DIMETHYL ETHER PRODUCT

CROSS-REFERENCE TO RELATED APPLICATIONS

This application is a national stage application under 35 U.S.C. § 371 of International Application No. PCT/CN2018/102072, filed Aug. 24, 2018, which claims priority to International Application No. PCT/CN2017/098861, filed Aug. 24, 2017, the disclosures of which are explicitly incorporated by reference herein.

FIELD OF THE INVENTION

This invention relates in general to a dehydration process and in particular to a process for the dehydration of methanol in the presence of a solid Brønsted acid catalyst and a promoter compound.

BACKGROUND OF THE INVENTION

Industrial processes for the dehydration of methanol to dimethyl ether using catalysts such as alumina are known. Such processes employing alumina catalysts are described, for example in EP-A-1396483. Although these alumina catalysts are solid acid catalysts they are not Brønsted acid catalysts.

Processes for the dehydration of alcohols such as methanol employing zeolite catalysts in dehydration reactions of methanol are described, for example in WO 2004/074228.

WO 2004/074228 describes a process for preparing dimethyl ether in high yield by employing a dual-catalyst system. Methanol is initially dehydrated over a hydrophilic solid acid catalyst such as gamma-alumina; unreacted methanol is then dehydrated over a second solid acid catalyst, a hydrophobic zeolite such as ZSM-5.

EP-A-1396483 and WO 2004/074228 exemplify the use of high reaction temperatures, typically 250° C. and higher. Whilst the use of such high reaction temperatures may be desirable to achieve acceptable reaction rates, a disadvantage is that at temperatures, typically in excess of 250° C., hydrocarbons are co-produced with the dimethyl ether product and this typically leads to a reduction in catalytic performance.

WO 2011/027105 describes a process for the simultaneous dehydration of methanol and hydrolysis of methyl acetate. The process can be conducted at reaction temperatures below 250° C. by employing a zeolite having a 2-dimensional framework structure comprising at least one channel having a 10-membered ring. Examples of such zeolites are zeolites of framework type FER typified by ferrierite and HEU typified by clinoptilolite.

Processes for the co-production of acetic acid and dimethyl ether by the dehydration of methanol and hydrolysis of methyl acetate in the presence of zeolites having a 2-dimensional framework structure are also described, for example in WO 2013/124404 and WO 2013/124423.

Processes in which methanol-containing streams are dehydrated over various types of solid acid catalyst such as heteropolyacids, gamma-aluminas or zeolites are described, for example in WO 2015/193186 and WO 2015/193188.

SUMMARY OF THE INVENTION

Applicant has now found that compounds which are (i) ketones of Formula I $R^1COR^2$ wherein $R^1$ and $R^2$ are identical or different and are each a $C_1$-$C_{11}$ alkyl group, and furthermore $R^1$ and $R^2$ together with the carbonyl carbon atom to which they are bonded may form a cyclic ketone or (ii) ketal derivatives of ketones of Formula I, have a beneficial effect on the rate of dehydration of methanol reactions carried out in the presence of solid Brønsted acid catalysts which are aluminosilicate zeolites or heteropolyacids.

Accordingly, the present invention provides a process for dehydrating methanol to dimethyl ether product in the presence of a catalyst and a promoter, wherein the catalyst is at least one solid Brønsted acid catalyst selected from aluminosilicate zeolites or heteropolyacids, and the promoter is at least one (i) ketone of formula $R^1COR^2$ (Formula I)

wherein $R^1$ and $R^2$ are identical or different and are each a $C_1$-$C_{11}$ alkyl group and furthermore $R^1$ and $R^2$ together with the carbonyl carbon atom to which they are bonded may form a cyclic ketone; or (ii) ketal derivative of a ketone of Formula I; and wherein the molar ratio of promoter to methanol is maintained at 0.5 or less.

Advantageously, the promoters of the present invention allow productivity to dimethyl ether product to be improved in methanol dehydration reactions which are carried out in the presence of solid Brønsted acid catalysts which are aluminosilicate zeolites or heteropolyacids.

Also, according to the present invention there is provided a method of improving the productivity to dimethyl ether product in a process for dehydrating methanol in the presence of a catalyst and a promoter, wherein the catalyst is at least one solid Brønsted acid catalyst selected from aluminosilicate zeolites or heteropolyacids, and the promoter is at least one (i) ketone of formula $R^1COR^2$ (Formula I)

wherein $R^1$ and $R^2$ are identical or different and are each a $C_1$-$C_{11}$ alkyl group and furthermore $R^1$ and $R^2$ together with the carbonyl carbon atom to which they are bonded may form a cyclic ketone; or (ii) ketal derivative of a ketone of Formula I; and wherein the molar ratio of promoter to methanol is maintained at 0.5 or less.

Yet further according to the present invention there is provided the use of a promoter in a process for the catalytic dehydration of methanol to dimethyl ether to improve productivity to dimethyl ether product wherein the catalyst is at least one solid Brønsted acid catalyst selected from aluminosilicate zeolites or heteropolyacids, and the promoter is at least one (i) ketone of formula $R^1COR^2$ (Formula I)

wherein $R^1$ and $R^2$ are identical or different and are each a $C_1$-$C_{11}$ alkyl group and furthermore $R^1$ and $R^2$ together with the carbonyl carbon atom to which they are bonded may form a cyclic ketone; or (ii) ketal derivative of a ketone of Formula I; and wherein the molar ratio of promoter to methanol is maintained at 0.5 or less.

More advantageously, use of the ketones of Formula I in which at least one of $R^1$ and $R^2$ is a branched alkyl chain group may also mitigate deactivation of a zeolite catalyst thereby improving stability of a zeolite catalyst.

A further aspect of the present invention provides a process for dehydrating methanol to dimethyl ether product in the presence of a catalyst, wherein the catalyst is at least one solid Brønsted acid catalyst selected from aluminosilicate zeolites or heteropolyacids, and wherein prior to using the catalyst in the dehydration process, the catalyst has been impregnated with a promoter, wherein the promoter is at least one (i) ketone of formula R1COR2 (Formula I)
wherein R1 and R2 are identical or different and are each a C1-C7 C11 alkyl group and furthermore R1 and R2 together with the carbonyl carbon atom to which they are bonded may form a cyclic ketone; or (ii) ketal derivative of a ketone of Formula I.

BRIEF DESCRIPTION OF THE DRAWINGS

FIG. 1 depicts STY to dimethyl ether in the dehydration of methanol in the presence of the zeolite ZSM-5 as catalyst and in the presence of the ketone compounds, di-n-propyl ketone and di-iso-propyl ketone.

DETAILED DESCRIPTION OF THE INVENTION

The catalytic dehydration reaction of methanol can be represented by the following equation: 2 methanol⇌dimethyl ether+water.

In the present invention, the dehydration process is carried out in the presence of at least one solid Brønsted acid catalyst which is an aluminosilicate zeolite or a heteropolyacid as the catalyst. As would be understood by the skilled person in the art, by 'Brønsted acid catalyst' is meant an acid catalyst which has the ability to donate an acidic proton to facilitate a chemical reaction.

Aluminosilicate zeolites are crystalline microporous materials which have framework structures constructed from tetrahedra of $SiO_4$ and $AlO_4$ that share vertices. Such tetrahedral species are generally referred to as $TO_4$ species wherein the T atom is silicon or aluminium. Aluminium 'T' atoms can be partially or wholly replaced by one or more gallium, boron or iron atoms. For the purposes of the present invention, such gallium, boron or iron modified zeolites are considered to fall within the definition of the term 'aluminosilicate zeolites'.

Silicoaluminophosphate structures containing $PO_4$ tetrahedra are not considered to be aluminosilicate materials and consequently, such silicoaluminophosphates, for example SAPO-type materials, are not within the scope of the present invention.

A zeolite framework topology contains a regular array of pores, channels and/or pockets that vary in size, shape and dimensionality. These framework topologies or structure types of zeolites are assigned three-letter structure codes by the Structure Commission of the International Zeolite Association, under the authority of IUPAC.

A description of zeolites, their framework codes, structure, dimensionality, properties and methods of synthesis can be found in *The Atlas of Zeolite Framework Types* (C. Baerlocher, W. M. Meier, D. H. Olson, 5$^{th}$ Ed. Elsevier, Amsterdam, 2001) in conjunction with the web-based version (http.//www.iza-structure org/databases/).

Zeolite crystals contain pore or channel systems of molecular dimensions with fixed geometry and size and can be classified according to the number of channels running in different directions within the zeolite framework structure. A zeolite is described as 1-dimensional, 2-dimensional or 3-dimensional if the zeolite has one, two or three channels in different directions, respectively. Zeolites for use in the present invention may possess a 1-dimensional, a 2-dimensional or a 3-dimensional framework structure.

In some or all embodiments of the present invention the Brønsted acid catalyst is a zeolite which zeolite has a 1-dimensional framework structure. Specific non-limiting examples of such zeolites include zeolites selected from framework types MOR, MTT and TON. Examples of zeolites having framework type MOR include mordenite. Examples of zeolites having framework type MTT include ZSM-23. Examples of zeolites having framework type TON include ZSM-22 and theta-1.

In some or all embodiments of the present invention the Brønsted acid catalyst is a zeolite which zeolite has a 2-dimensional framework structure. Specific non-limiting examples of such zeolites include zeolites selected from framework types MWW or FER. Examples of zeolites having framework type MWW include PSH-3 and MCM-22. Examples of zeolites having framework type FER include ferrierite and ZSM-35.

In some or all embodiments of the present invention the Brønsted acid catalyst is a zeolite which zeolite has a 3-dimensional framework structure. Specific non-limiting examples of such zeolites include zeolites selected from framework types MFI, FAU, CHA and BEA. Examples of zeolites of framework type MFI include ZSM-5. Examples of zeolites of framework type FAU include zeolite Y and zeolite X. Examples of zeolites of framework type CHA include chabazite, SSZ-13 and SSZ-62. Examples of zeolites of framework type BEA include zeolite beta and SSZ-26.

Zeolites may also be classified according to the size of their pores. Zeolites with pore openings limited by 8 T atoms in tetrahedral co-ordination are defined as "small pore zeolites" (8-membered rings). Zeolites with pore openings limited by 10 T atoms in tetrahedral co-ordination are defined as "medium pore zeolites" (10-membered rings). Zeolites with pore openings limited by 12 T atoms in tetrahedral co-ordination are defined as "large pore zeolites" (12-membered rings).

For use in the present invention the Brønsted acid catalyst is a zeolite which zeolite may be a small, medium or large pore zeolite.

In some or all embodiments of the present invention, the Brønsted acid catalyst is a zeolite which zeolite is a small pore zeolite. Specific non-limiting examples of small pore zeolites include those of framework type CHA.

In some or all embodiments of the present invention, the Brønsted acid catalyst is a zeolite which zeolite is a medium pore zeolite. Specific non-limiting examples of medium pore zeolites include those of the framework types FER, MFI, MWW, MTT and TON and also ITQ-type zeolites, such as ITQ-13 and ITQ-34

In some or all embodiments of the present invention, the Brønsted acid catalyst is a zeolite which zeolite is a large pore zeolite. Specific non-limiting examples of large pore zeolites include those of framework types, MOR, FAU, BEA, GME, IWW, MAZ, LTL and OFF and ITQ-type zeolites such as ITQ-7 and ITQ-26.

In some or all embodiments of the present invention, the Brønsted acid catalyst is a zeolite which zeolite is selected from zeolites of framework type FER, MWW, MTT, MFI, MOR, CHA, BEA and TON, such as the zeolites ferrierite, PSH-3, ZSM-23, ZSM-5, mordenite, SSZ-13, zeolite beta and ZSM-22 respectively.

Typically, zeolites are synthesised from synthesis mixtures comprising a silica source, an alumina source, alkali metal hydroxide and water in desired proportions. The synthesis mixture is maintained, with or without agitation, under temperature, pressure and time conditions sufficient to form a crystalline aluminosilicate zeolite. The resulting zeolite contains alkali metal as a cation. Such cations may be replaced by known ion-exchange techniques. For example, the zeolite may be contacted with aqueous solutions of ammonium salts to substitute ammonium ions for the alkali metal cations. Ammonium-form zeolites are also available commercially.

Whilst zeolites in their ammonium-form can be catalytically active, for use in the present invention it is preferred to utilise a zeolite in its hydrogen-form (H-form). H-form zeolites are commercially available. Alternatively, an ammonium-form zeolite can be converted to the H-form by known techniques, for example by calcination under air or an inert gas at high temperature.

In some or all embodiments of the present invention, the Brønsted acid catalyst is a zeolite which zeolite is a hydrogen-form (H-form) zeolite.

For use in the present invention, a zeolite may be composited with at least one binder material. The binder material may be a refractory inorganic oxide, such as silicas, aluminas, alumina-silicates, magnesium silicates, magnesium aluminium silicates, titanias and zirconias.

For use in the present invention, the relative proportions of zeolite and binder material in the composite may vary widely. Suitably, the binder material can be present in an amount of from 10% to 90% by weight of the composite.

For use in the present invention, the silica to alumina molar ratio of a zeolite may vary widely but suitably is in the range 10 to 300, for example in the range 20 to 280, such as in the range 20 to 100.

The promoter compounds of the present invention have also been found to beneficial in promoting methanol dehydration reactions which are catalysed by heteropolyacid catalysts.

The term "heteropolyacid" as used herein and throughout this specification is meant to include the free acids and salts thereof. Heteropolyacids for use in the present invention may be used either as free acids or as partial salts. Typically, the heteropolyacid, or the anionic component of its corresponding salt comprises 2 to 18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for example cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well-known anions are named after the original researchers in this field and are known, for example as Keggin, Wells-Dawson and Anderson-Evans-Perloff structures.

Heteropolyacids usually have a high molecular weight, for example in the range from 700-8500 and include dimeric complexes. They have a relatively high solubility in polar solvents such as water or other oxygenated solvents, especially if they are free acids and in the case of several salts, and their solubility can be controlled by choosing the appropriate counter-ions.

In some or all embodiments of the present invention, the Brønsted acid catalyst is a heteropolyacid which heteropolyacid is selected from silicotungstic acids, phosphotungstic acids and 12-tungstophosphoric acid ($H_3[PW_{12}O_{40}].xH_2O$); 12-molybdophosphoric acid ($H_3[PMo_{12}O_{40}].xH_2O$); 12-tungstosilicic acid ($H_4[SiW_{12}O_{40}].xH_2O$); 12-molybdosilicic acid ($H_4[SiMO_2O_{40}].xH_2O$) and salts thereof, for example ammonium salts of heteropolyacids, such as ammonium salts of a phosphotungstic acid or a silicotungstic acid.

In some or all embodiments of the present invention the Brønsted acid catalyst is a heteropolyacid which heteropolyacid is a silicotungstic acid.

Heteropolyacids for use in the present invention may be supported on any suitable support such as refractory inorganic oxides, for example silicas, aluminas and silica-aluminas.

Promoter compounds for use in the present invention are selected from (i) ketones of Formula I, $R^1COR^2$, wherein $R^1$ and $R^2$ are identical or different and each is a $C_1$-$C_{11}$ alkyl group, preferably a $C_1$-$C_2$ alkyl group, and furthermore $R^1$ and $R^2$ together with the carbonyl carbon atom to which they are bonded may form a cyclic ketone and (ii) ketal derivatives of ketones of Formula I.

In the present invention, a ketone of Formula I may be a straight alkyl chain ketone, a branched alkyl chain ketone or a cyclic ketone.

Advantageously, Applicant has found that the use of ketones of Formula I in which at least one of $R^1$ and $R^2$ is a branched chain alkyl group, in zeolite-catalysed methanol dehydration reactions can lead to improved stability of the catalyst compared to the use of the corresponding straight chain ketone.

Thus, further according to the present invention, there is provided the use of a ketone compound to improve productivity to dimethyl ether product and reduce catalyst deactivation in a process for the catalytic dehydration of methanol to dimethyl ether product wherein the catalyst is at least one aluminosilicate catalyst and the ketone compound is at least one ketone of formula $R^1COR^2$ wherein at least one of $R^1$ and $R^2$ is a branched chain $C_3$-$C_{11}$ alkyl group, such as a branched chain $C_3$-$C_7$ alkyl group, and suitably wherein each of $R^1$ and $R^2$ is a branched chain $C_3$-$C_{11}$ alkyl group, such as a branched chain $C_3$-$C_7$ alkyl group.

There is also provided a method of improving the productivity to dimethyl ether product and stability of a catalyst in a process for the catalytic dehydration of methanol to dimethyl ether product in the presence of a zeolite catalyst and a ketone compound wherein the catalyst is at least one aluminosilicate catalyst and the promoter is at least one ketone of formula $R^1COR^2$ wherein at least one of $R^1$ and $R^2$ is a branched chain $C_3$-$C_{11}$ alkyl group, such as a branched chain $C_3$-$C_7$ alkyl group, and suitably wherein each of $R^1$ and $R^2$ is a branched chain $C_3$-$C_{11}$ alkyl group, such as a branched chain $C_3$-$C_7$ alkyl group.

In some or all embodiments of the present invention, $R^1$ and $R^2$ are identical or different and each is a branched chain $C_3$-$C_{11}$ alkyl group, preferably a branched chain $C_3$-$C_7$ alkyl group.

In some or all embodiments of the present invention, $R^1$ and $R^2$ are identical or different and each is a $C_1$-$C_3$ alkyl group.

In some or all embodiments of the present invention, one or both of $R^1$ and $R^2$ is a $C_3$ alkyl group and the $C_3$ alkyl group is a straight chain or branched chain $C_3$ alkyl group.

Suitably, in these embodiments $R^1$ and $R^2$ are each a $C_3$ branched chain alkyl group and the ketone of Formula I is 2,4-dimethyl-3-pentanone.

In some or all embodiments of the present invention, $R^1$ and $R^2$ are identical and each is a $C_3$-$C_{11}$ alkyl group, preferably a $C_3$-$C_7$ alkyl group, for example n-propyl, isopropyl, n-butyl, isobutyl, tert-butyl, pentyl, hexyl or heptyl group.

Specific non-limiting examples of ketones suitable for use in the present invention wherein $R^1$ and $R^2$ are identical are acetone, 3-pentanone, 4-heptanone and 5-nonanone.

In some or all embodiments of the present invention, $R^1$ and $R^2$ are different, wherein $R^1$ is a $C_1$-$C_3$ alkyl group and $R^2$ is a $C_1$-$C_7$ alkyl group. Suitably, in these embodiments, $R^1$ is a $C_1$ alkyl group and $R^2$ is a $C_1$-$C_3$ alkyl group.

Specific non-limiting examples of ketones suitable for use in the present invention wherein $R^1$ and $R^2$ are different are 2-butanone, 2-heptanone and 2-nonanone.

In some or all embodiments of the present invention, the ketone of Formula I is a cyclic ketone and is suitably selected from cyclic ketones comprising 4 to 12 carbon atoms, for example 4 to 6 carbon atoms. Specific non-limiting examples of cyclic ketones of Formula I are cyclobutanone, cyclopentanone and cyclohexanone.

The extent to which a dehydration reaction is promoted may vary depending on factors such as the structure of the zeolite and nature of the promoter employed in the reaction. Desirably, to promote increased productivity to dimethyl ether, the channels of a zeolite must be of a size such that a promoter is able to diffuse freely through the zeolite channels. Thus, for larger promoter compounds, it is preferred to utilise medium or large pore zeolites.

It has been found that promotion of the dehydration reaction tends to be greater for large pore zeolites wherein in Formula I, $R^1$ and $R^2$ are identical and are of longer alkyl chain length. Thus, in some or all embodiments of the present invention, the Brønsted acid catalyst is a zeolite which zeolite is a large pore zeolite, $R^1$ and $R^2$ are identical and each is a $C_3$-$C_{11}$ alkyl group, preferably a $C_3$-$C_7$ alkyl group, for example a $C_3$ alkyl group. Suitably, in these embodiments, the large pore zeolite is selected from framework types MFI, BEA and MOR, for example ZSM5, zeolite beta, and mordenite respectively.

Typically, promotion of the dehydration reaction in the presence of medium pore zeolites has been found to be more desirable with shorter alkyl chain groups. Thus, in some or all embodiments of the present invention, the Brønsted acid catalyst is a zeolite which zeolite is a medium pore zeolite, $R^1$ and $R^2$ are identical or different and each is a $C_1$-$C_2$ alkyl group, for example a C1 alkyl group. Suitably, in these embodiments, the medium pore zeolite is selected from framework types FER, MWW, MTT and TON, for example ferrierite, ZSM-35, PSH-3, ZSM-23 and ZSM-22.

Ketal derivatives of the ketones of Formula I also function as promoters in the present invention. In the present invention, the term 'ketal derivative' also includes the hemi-ketal derivatives of the ketones of Formula I. As would be readily understood by a person skilled in the art, a ketal is a functional group derived from a ketone by replacement of the carbonyl group of the ketone by two alkoxy groups. A hemi-ketal is derived from a ketone by replacement of the carbonyl group of the ketone by an alkoxy group and a hydroxyl group. Consequently, the ketal derivatives of the ketones of Formula I may be represented by the general structural formula:

(Formula II)

wherein $R^1$ and $R^2$ are identical or different and each is a $C_1$ to $C_{11}$ alkyl group, preferably a $C_1$ to $C_7$ alkyl group, and furthermore $R^1$ and $R^2$ together with the carbonyl carbon atom to which they are bonded may form a cyclic ketone and each of $R^3$ and $R^4$ is an alkyl group or hydrogen with the proviso that $R^3$ and $R^4$ are not both hydrogen.

Suitably, each of $R^3$ and $R^4$ is an alkyl group which alkyl group is a $C_1$ to $C_6$ straight or branched chain alkyl group. In these instances, $R^3$ and $R^4$ may be identical or different.

In some or all embodiments of the present invention, $R^3$ and $R^4$ are each selected from a $C_1$ or $C_2$ alkyl group. In these embodiments $R^3$ and $R^4$ may be identical or different.

In some or all embodiments of the present invention, $R^3$ and $R^4$ are identical and each is a $C_1$ alkyl group. In this instance the ketal of Formula II is a dimethoxy ketal. Specific non-limiting examples of dimethoxy ketals are 2,2-dimethoxypropane and 2,2-dimethoxybutane.

In some or all embodiments of the present invention, the ketal derivative of the ketone of Formula I is a hemi-ketal. Suitably, in these embodiments one of $R^3$ and $R^4$ is hydrogen and one of $R^3$ and $R^4$ is a $C_1$ to $C_6$ alkyl group, for example a $C_1$ to $C_3$ alkyl group.

In some or all embodiments of the present invention, the ketone of Formula I is a cyclic ketone which cyclic ketone has 4 to 12 carbon atoms, for example 4 to 6 carbon atoms and $R^3$ and $R^4$ of the ketal derivative of the cyclic ketone are each a $C_1$ to $C_2$ alkyl group and may be identical or different. Suitably, in these embodiments, $R^3$ and $R^4$ are identical and may be a $C_1$ alkyl group.

Specific examples of ketal derivatives of cyclic ketones of Formula I include cyclohexanone dimethyl ketal.

Examples of suitable ketones of Formula I from which the ketal derivatives of Formula II are derived include the following compounds: methyl ethyl ketone, diethyl ketone, methyl isopropyl ketone, 2,4-dimethyl-3-pentanone, 2-heptanone, 4-heptanone and 5-nonanone.

Mixtures of ketones of Formula I and the ketal derivatives of Formula II may also be used in the present invention.

Ketones of Formula I and their ketal derivatives are available commercially.

In the present invention, a promoter may be added as a component of the feed to the dehydration process. Alternatively and/or additionally, a promoter may be generated in-situ by the addition to the process of any compound (a precursor compound) from which a ketone of Formula I or a ketal derivative thereof can be generated in-situ.

Suitable precursor compounds for the generation of the ketone compounds of Formula I include the ketal derivatives thereof.

The ketone compounds of Formula I may also be generated in-situ via retro aldol-type condensation reactions of β-hydroxyketone compounds. For example, where it is desired to generate acetone in-situ in the dehydration process, the precursor compound may be the β-hydroxyketone, 4-hydroxy-4-methyl-3-pentan-2-one.

In some or all embodiments of the present invention, a promoter precursor compound is a β-hydroxyketone compound or a compound resulting from loss of water therefrom.

In the present invention the molar ratio of promoter to methanol is maintained throughout the dehydration reaction at 0.5 or less. In some or all embodiments of the present invention the molar ratio of promoter to methanol is maintained in the range 0.00001:1 to 0.2:1. Non-limiting examples of suitable molar ratio ranges of promoter to methanol include 0.00002 to 0.2:1, 0.00005 to 0.2:1, 0.0001 to 0.2:1, 0.0005 to 0.2:1, 0.001 to 0.2:1, 0.002 to 0.2:1, 0.005 to 0.2:1, 0.01 to 0.2:1, and 0.02:1 to 0.2:1.

Suitably, in the present invention the total amount of promoter relative to the total amount of methanol is maintained throughout the dehydration reaction in an amount of at least 1 ppm. In some or all embodiments of the present invention, the total amount of promoter relative to the total amount of methanol is maintained throughout the dehydration reaction in an amount of at least 0.0005 mol %, for example in an amount of 0.0005 mol % to less than 50 mol %, such as 0.0005 mol % to 20 mol %, for instance 0.001 mol % to 20 mol %. In some or all embodiments of the present invention, the total amount of promoter relative to the total amount of methanol is maintained throughout the dehydration reaction in an amount of at least 0.01 mol %, for example in an amount of 0.01 mol % to less than 50 mol %, such as 0.01 mol % to 20 mol %, for instance 0.05 to 20 mol %. In some or all embodiments of the present invention, the total amount of promoter relative to the total amount of methanol is maintained throughout the dehydration reaction in an amount of at least 0.1 mol %, for example in an amount of 0.25 to less than 50 mol %, such as 0.25 mol % to 20 mol %.

In some or all embodiments of the present invention, the promoter is a ketone of Formula I, suitably a ketone of Formula I in which $R^1$ and $R^2$ are each a straight chain $C_1$ to $C_7$ alkyl group, suitably a $C_1$ to $C_3$ alkyl group and suitably wherein the concentration of promoter relative to methanol is maintained in an amount of 0.25 to 20 mol % and the Brønsted acid catalyst is a zeolite which zeolite is a medium pore zeolite, suitably selected from zeolites of framework type FER, MWW and TON, such as ferrierite, PSH-3 and ZSM-22 respectively or a large pore zeolite, suitably of framework type MFI, MOR and BEA for example ZSM-5, mordenite and zeolite beta respectively. In these embodiments, the zeolite may have a silica to alumina molar ratio in the range 1 to 300, for example in the range 20 to 280, suitably in the range 20 to 100.

In some or all embodiments of the present invention, the promoter is a ketal derivative of a ketone of Formula I, suitably a dimethoxyketal, for example 2,2-dimethoxybutane and 2,2-dimethoxypropane. Suitably, in these embodiments, the concentration of promoter relative to methanol is maintained in an amount of 0.25 to 20 mol % and the Brønsted acid catalyst is a zeolite which zeolite is a medium pore zeolite, suitably selected from zeolites of framework type FER, MWW and TON, such as ferrierite, PSH-3 and ZSM-22 respectively or a large pore zeolite, suitably of framework type MFI and BEA for example ZSM-5 and zeolite beta respectively. In these embodiments, the zeolite may have a silica to alumina molar ratio in the range 20 to 280, suitably in the range 20 to 100.

In some or all embodiments of the present invention, the promoter is a ketone of Formula I, suitably a ketone of Formula I wherein $R^1$ and $R^2$ are identical and are each a $C_2$-$C_7$ alkyl group, preferably a $C_2$-$C_3$ alkyl group, and suitably a straight chain alkyl group and suitably wherein the concentration of promoter relative to methanol is maintained in an amount of 0.25 to 20 mol %, for example 2 to 20 mol %, and the Brønsted acid catalyst is a heteropolyacid which heteropolyacid is suitably a silicotungstic acid.

In some or all embodiments of the present invention, the solid Brønsted acid catalyst may be impregnated with the promoter prior to being used in the dehydration process. The method of impregnation is not limited and any technique known in the art may be used, for example, incipient wetness technique or excess solution technique. The incipient wetness technique is so-called because it requires that the volume of impregnating solution be predetermined so as to provide the minimum volume of solution necessary to just wet the entire surface of the support, with no excess liquid. The excess solution technique as the name implies, requires an excess of the impregnating solution, the solvent being thereafter removed, usually by evaporation. The promoter may be used as the impregnation solution directly, or a dilute solution of the promoter may be used. When a dilute solution of promoter is used, the solvent for the impregnation solution may suitably be an aqueous solution, an organic solution, or a mixture of aqueous and organic solvent(s), depending upon the solubility of the promoter being used; non-limiting examples of suitable solvents include water, alcohols, for example methanol, ethers, and mixtures thereof, such as aqueous alcoholic solutions, for example an aqueous methanol solution.

Suitably, in the present invention, the dehydration process may be carried out as a standalone process. In such cases the dehydration reaction is not, for example carried out as part of a co-production process, such as co-production processes for the production of acetic acid and dimethyl ether by dehydration of methanol and hydrolysis of a methyl acetate co-feed. Thus, suitably, in the present invention, the feed components to the process are methanol and at least one compound selected from promoter compounds and promoter precursor compounds.

However, typically, the product stream of the methanol dehydration reaction will comprise dimethyl ether, water, unconverted methanol and one or more compounds selected from promoter and promoter precursor compounds. Thus, in some or all embodiments of the present invention, one or more components of the product stream of the dehydration process are recycled as feed to the process. In such instances one or both of dimethyl ether and water are additional feed components to the dehydration process.

Thus, in some or all embodiments of the present invention the feed components to the dehydration process are methanol, at least one promoter compound and one or both of dimethyl ether and water.

In instances where it is desired to generate the promoter in situ in the dehydration process the feed components to the process may be methanol and at least one precursor compound of a promoter compound.

Thus, in some or all embodiments of the present invention the feed components to the dehydration process are methanol, one or both of (i) at least one promoter compound and (ii) at least one precursor compound of a promoter compound; and one or both of dimethyl ether and water.

The feed components to the process may be supplied to the process in one or more feed streams.

Preferably, methyl acetate is not a component of the feed to the process.

The dehydration process is carried out as a heterogeneous process, either as a vapour phase heterogeneous process or as a liquid phase heterogeneous process.

The type of reactor used for the dehydration process is not limited, and it may be suitably carried out in any type of reactor within which a vapour phase heterogeneous process or a liquid phase heterogeneous process may be performed. Non-limiting types of reactors with which the dehydration reaction may be performed include tank reactors, multi-tubular reactors, plug-flow reactors, loop reactors, fluidized bed reactors, and reactive distillation columns.

The dehydration process may be carried out at a temperature of from 100 to 300° C. In some or all embodiments of the present invention, the dehydration process is carried out at a temperature of from 140 to 250° C., for example from 150 to 250° C.

Suitably, the dehydration process may be carried out at atmospheric pressure or at elevated pressure.

In some or all embodiments of the present invention, the dehydration process is carried out at a total pressure of atmospheric pressure to 3000 kPa. Where the process is conducted in the liquid phase, higher total pressures, such as 4000 kPa to 10,000 kPa, may be required to maintain the dimethyl ether product in solution.

In some or all embodiments of the present invention, the dehydration process is carried out as a heterogeneous vapour phase process at a total pressure of atmospheric pressure to 3000 kPa. In these embodiments, the temperature may be from 100 to 300° C., such as from 140 to 250° C., for example from 150 to 250° C.

For vapour phase processes, the process may be carried out at a total gas hourly space velocity (GHSV) in the range 500 to 40,000 $h^{-1}$.

For liquid phase processes, the process may be carried out at a total liquid hourly space velocity (LHSV) in the range 0.2 to 20 $h^{-1}$.

The dehydration process may be carried out using one or more beds of zeolite catalyst, suitably selected from fixed bed, fluidised bed, and moving beds of catalyst.

The dehydration process may be operated as either a continuous or a batch process, preferably as a continuous process.

The dehydration process generates a crude reaction product comprising dimethyl ether and water as reaction products, unreacted methanol and one or compounds selected from promoter compounds and promoter precursor compounds. One or more components of the crude reaction product may be recycled as feed to the process.

Dimethyl ether may be recovered from the crude reaction product by any suitable method, for example by distillation methods.

Without being bound by theory, the productivity of catalysts will typically decrease over time on stream; in industrially applied catalytic processes, one of the ways by which the decrease in productivity may be compensated for is by increasing the reaction temperature to maintain a consistent productivity. A disadvantage of increasing the temperature of the reaction is that this may lead to an increase in undesirable by-products or may result in a decrease in selectivity; another disadvantage of increasing the temperature of the reaction is that such an increase in temperature may accelerate the rate of catalyst deactivation. However, without wishing to be bound by theory, it is believed that in the present invention, decreases in productivity of the catalyst may be at least in part compensated for by increasing the relative concentration of the promoter in the methanol feed, and thus may reduce or eliminate the need for an increase in temperature to compensate for any reduction in productivity which may occur with time on stream; similarly, decreases in productivity of the catalyst may be at least in part compensated for by changing the promoter used or by adding a second or further additional promoter compound to the methanol feed as the time on stream increases.

In addition to the beneficial effect on the rate of dehydration of methanol reactions carried out in the presence of solid Brønsted acid catalysts selected from aluminosilicate zeolites or heteropolyacids, it is believed that the use of promoters as described herein may result in an increase in the stability of the solid Brønsted acid catalyst and may make the solid Brønsted acid catalyst more resistant to deactivation by impurities present in the methanol feed.

In a further aspect of the present invention provides a process for dehydrating methanol to dimethyl ether product in the presence of a catalyst, wherein the catalyst is at least one solid Brønsted acid catalyst selected from aluminosilicate zeolites or heteropolyacids, and wherein prior to using the catalyst in the dehydration process, the catalyst has been impregnated with a promoter, wherein the promoter is at least one (i) ketone of formula R1COR2 (Formula I)

wherein R1 and R2 are identical or different and are each a C1-C7 C11 alkyl group and furthermore R1 and R2 together with the carbonyl carbon atom to which they are bonded may form a cyclic ketone; or (ii) ketal derivative of a ketone of Formula I.

In this further aspect of the invention, the feed to the dehydration process comprises methanol and may optionally comprise other components, for example dimethyl ether, water, or at least one compound which is a promoter compound of Formula I or a ketal derivative of a ketone of Formula I.

The invention is now illustrated with reference to the following non-limiting Examples.

EXAMPLES

Details of the catalysts used in the Examples are provided in Table 1 below. In Table 1, only ring sizes of 8 T atoms or greater are given. Smaller ring sizes have been omitted.

TABLE 1

| Catalyst | Framework Code | Framework Structure | Ring Size | SAR |
|---|---|---|---|---|
| Zeolite beta | BEA | 3-D | 12 | 25 |
| Zeolite Y | FAU | 3-D | 12 | 30 |
| Mordenite | MOR | 1-D | 12 | 20 |
| ZSM-22 | TON | 1-D | 10 | 69 |
| ZSM-5 | MFI | 3-D | 10 | 23 |
| SSZ-13 | CHA | 3-D | 8 | 24 |
| Ferrierite | FER | 2-D | 10.8 | 20 |
| PSH-3 | MWW | 2-D | 10 | 21 |
| STA | n/a | n/a | n/a | n/a |
| Gamma-alumina | n/a | n/a | n/a | n/a |

SAR indicates the silica: alumina molar ratio
1-D, 2-D and 3-D indicate a 1-dimensional, a 2-dimensional and a 3-dimensional zeolite framework structure respectively
STA is silicotungstic acid and utilised in the dehydration reactions supported on silica.
n/a means not applicable Examples 1 to 6

Unless otherwise specified, all zeolites used in Examples 1 to 6 were utilised in the methanol dehydration reactions in their H-form.

Zeolite Y was obtained in H-form from Zeolyst International. All other zeolites (except ZSM-22 and MCM-41) were obtained in ammonium-form from Zeolyst International and converted to H-form by calcination in air at 500° C. The zeolite MCM-41(hexagonal) was obtained from Sigma-Aldrich and converted to H-form by calcination in air at 500° C.

The gamma-alumina used in Examples was SAS 200 gamma-alumina obtained from BASF AG.

Preparation of H-ZSM-22 and silica-supported silicotungstic acid were carried out in accordance with the methods described below.

The ketones and ketal derivatives used in Examples 1 to 6 were obtained from Sigma-Aldrich or Fisher Scientific.

Preparation of H-ZSM-22

For use in the preparation of the zeolite the following solutions were prepared:
i) aluminium chlorohydrol solution (25.3 g aluminium chlorohydrol in 253 g of deionised water);
ii) potassium hydroxide solution (82 g 88.8% potassium hydroxide in 820 g of deionised water);
iii) Ludox solution (900 g Ludox AS40 (silica sol with 40 wt % $SiO_2$ stabilised with ammonium hydroxide ex Aldrich) diluted in 2694 g of deionised water);
iv) ammonium chloride (200.6 g ammonium chloride in 3750 g deionised water)

The aluminium chlorohydrol solution was added slowly with vigorous stirring to the potassium hydroxide solution of to form an aluminate solution. 226 g diaminohexane (DAH) was added to the aluminate solution. The DAH/aluminate solution was added to the Ludox solution under vigorous stirring and stirred for at least 30 minutes until a gel formed. The gel was transferred to an autoclave and agitated (500 rpm) at a temperature of 160° C. for 48 hours to form a slurry. The autoclave was allowed to cool, under agitation, to a temperature below 60° C. and the slurry centrifuged to separate the solids from the mother liquor. The solids were washed with sufficient deionised water such that the pH of was less than 8 and then dried overnight at a temperature of 110° C. to generate a dried zeolitic material. The X-ray diffraction pattern of the zeolitic material showed it to be ZSM-22. The dried zeolitic material was calcined at 600° C. for 12 hours to effect removal of the diaminohexane from the pores of the pores of the zeolite. The calcined zeolite was converted into the ammonium-form of the zeolite by ion-exchange with the ammonium chloride solution at a temperature of 80° C. for 4 hours and then repeated. The ion-exchanged zeolite was separated from the liquid by filtration, washed with deionised water and dried overnight at 110° C. The ammonium-exchanged zeolite was converted to the H-form by calcination in air at 500° C. for 8 hours.

Preparation of Silica-Supported Silicotungstic Acid Catalyst 30.1 g silica (ex Grace Chemicals) was added to a solution of 14.30 g silicotungstic acid (ex Nippon Organic Chemicals) in 39.9 g water. The silica/silicotungstic acid solution was left to stand for 30 minutes before being oven dried at a temperature of 120° C. for a period of 16 hours. The dried catalyst material was then cooled to 50° C. 40.93 g catalyst was obtained which contained 19.5 wt % of tungsten.

General Reaction Method and Apparatus

The methanol dehydration reactions were carried out using a 16-channel parallel fixed-bed stainless steel reactor system. Each reactor (2 mm internal diameter) housed a 25 mg bed of catalyst (having particle size fraction of 100 to 200 microns diameter) loaded on top of a 6 cm deep bed of an inert material (carborundum). The reactor volume above the catalyst was also packed with carborundum.

Each reactor was maintained at a temperature of 150° C. and at a total pressure of 1100 kPa throughout the reactions. A gaseous feed comprising 10 mol % methanol and inert gas was introduced into the reactor and allowed to flow through the catalyst bed for a period of 48 hours at which point a promoter compound was added to the feed to achieve a gaseous feed comprising 10 mol % methanol and 2 mol % promoter compound (relative to methanol). The gaseous feed comprising the promoter was introduced into the reactor for a period of 24 hours at a constant flow rate of methanol of 13 mmol $h^{-1}$ and a constant promoter flow rate of 0.27 mmol h.

The effluent stream from each reactor was diluted with inert gas (nitrogen) and was periodically analysed by online gas chromatography to determine the yield of dimethyl ether product.

Example 1

This Example demonstrates the effect of various promoter compounds on methanol dehydration reactions employing various catalysts.

The methanol dehydration reactions were carried out using the General Reaction Method and Apparatus described above utilising the promoter compounds and catalysts specified in Table 2 below. The observed space time yields to dimethyl ether product are provided in Table 2. In Table 2, DME=dimethyl ether; MEK=butanone; DEK=3-pentanone; DnPK=4-heptanone; and DiPK=2,4-dimethyl-3-pentanone

TABLE 2

| | DME STY/g $kg^{-1}$ $h^{-1}$ for different promoters | | | | | |
|---|---|---|---|---|---|---|
| Catalyst | No promoter | Acetone | MEK | DEK | DnPK | DiPK |
| ferrierite | 2588 | 4154 | 3307 | — | — | — |
| ZSM-5 | 905 | 2228 | 2936 | 3789 | 5223 | 1177 |
| mordenite | 886 | 1132 | 1570 | 1283 | 3729 | 2155 |
| PSH-3 | 864 | 4837 | 3844 | 1545 | 1610 | 1467 |
| ZSM-22 | 320 | 924 | 750 | 465 | 648 | 356 |
| zeolite beta | 240 | 416 | 1373 | 1975 | 3006 | 852 |
| zeolite Y | 45 | 77 | 123 | 96 | 107 | 175 |
| SSZ-13 | 1448 | — | — | — | — | 1624 |
| STA | 615 | — | — | 920 | 1011 | — |

As Table 2 shows, in the presence of the ketone compounds, the space time yields to dimethyl ether were seen to increase where an aluminosilicate zeolite or a heteropolyacid catalyst was used in the reactions. However, no increase in dimethyl ether productivity was observed in those reactions which were carried out in the absence of a ketone compound.

Example 2

This Example demonstrates the effect of various promoter concentrations on zeolite-catalysed methanol dehydration reactions.

The methanol dehydration reactions were carried out using the General Reaction Method and Apparatus described above in the presence of the catalysts and at the acetone concentrations specified in Table 3 below. The various promoter concentrations (relative to methanol) were achieved by adjusting the flow rate of acetone to be in the range 0.03 mmol $h^{-1}$ to 2.7 mmol $h^{-1}$ depending on the desired promoter concentration to be achieved.

The observed space time yields to dimethyl ether product are provided in Table 3.

TABLE 3

| Relative promoter concentration (mol %) | Dimethyl ether STY/g kg$^{-1}$ h$^{-1}$ | | |
|---|---|---|---|
| | ferrierite | PSH-3 | ZSM-22 |
| 0 | 2555 | 815 | 327 |
| 0.25 | 2793 | 2370 | 475 |
| 0.50 | 3060 | 3095 | 563 |
| 1 | 3475 | 3950 | 701 |
| 2 | 4131 | 4892 | 923 |
| 5 | 5180 | 5939 | 1121 |
| 10 | 5947 | 6449 | 1295 |
| 15 | 6199 | 6397 | 1356 |
| 20 | 6481 | 6455 | 1452 |

As can be seen from an inspection of Table 3, the ketone compounds of the present invention can be used at a wide range of concentrations to provide an increase in space time yield to dimethyl ether in methanol dehydration reactions.

Example 3

This Example demonstrates the effect of ketal compounds on the catalytic dehydration of methanol.

Methanol dehydration reactions were carried out using the General Reaction Method and Apparatus described above in the presence of the ketal, 2,2-dimethoxybutane and the catalysts identified in Table 4 below. The observed space time yields to dimethyl ether product are provided in Table 4.

TABLE 4

| Catalyst | Dimethyl ether STY g kg$^{-1}$ h$^{-1}$ | |
|---|---|---|
| | No promoter | 2,2-DMB |
| ferrierite | 2622 | 3511 |
| mordenite | 926 | 1432 |
| ZSM-5 | 898 | 2667 |
| PSH-3 | 870 | 4383 |
| ZSM-22 | 333 | 1025 |
| zeolite beta | 246 | 1529 |
| zeolite Y | 44 | 81 |
| gamma-alumina | 2 | 2 |

2,2-DMB = 2,2-dimethoxybutane

As can be seen from Table 4, the addition of the ketal compound provided increased productivity to dimethyl ether in those reactions carried out using a zeolite catalyst. However, no increase in dimethyl ether productivity was observed in those reactions in which the reaction was carried out in the absence of the ketal or which were carried out in the presence of the ketal compound and gamma-alumina catalyst.

Example 4

This Example demonstrates the effect of various ketone compounds on the catalytic dehydration of methanol in the presence of ZSM-5 of various silica:alumina molar ratios (SAR).

The methanol dehydration reactions were carried out using the General Reaction Method and Apparatus described above and utilising the ketone compounds identified in Table 5 below. The observed space time yields to dimethyl ether product are provided in Table 5.

TABLE 5

| | Dimethyl ether STY/g kg$^{-1}$ h$^{-1}$ | | |
|---|---|---|---|
| Promoter | ZSM-5 SAR 23 | ZSM-5 SAR 80 | ZSM-5 SAR 280 |
| no promoter | 905 | 409 | 102 |
| acetone | 2228 | 3368 | 1132 |
| 2-butanone | 2936 | 2882 | 918 |
| 3-pentanone | 3789 | 3753 | 1426 |
| 4-heptanone | 5223 | 5872 | 2436 |
| 2,4-dimethyl-3-pentanone | 1177 | 978 | 317 |

As can be seen from an inspection of Table 5, the use of the straight and branched chain ketone compounds enabled an increase in dimethyl ether productivity to be achieved in reactions utilising zeolite catalysts of different silica:alumina molar ratios.

Example 5

In this Example, the effect of the straight chain di-n-propyl ketone and the branched chain di-iso-propyl ketone was investigated in methanol dehydration reactions employing the zeolite ZSM-5.

The methanol dehydration reactions were carried out using the General Reaction Method and Apparatus described above and employing the ketone promoters at a concentration of 2 mol % relative to methanol.

The results of this Example are shown in FIG. 1, wherein the circles represent periods in which methanol was used as the feed to the process i.e. no ketone addition. The black squares represent periods in which 5 mol % of di-n-propyl ketone (relative to methanol) was present in the methanol feed and the white squares represent periods in which 5 mol % of di-iso-propyl ketone (relative to methanol) was present in the methanol feed. As is illustrated in FIG. 1, during the periods in which a ketone compound was used, the space time yield (STY) to dimethyl ether was observed to increase compared to the periods carried out in the absence of the ketone compound. It was also observed that the use of the branched chain ketone, di-iso-propyl ketone, resulted in little or no catalyst deactivation at the concentration of promoter tested.

Example 6

This Example demonstrates the effect of various promoter concentrations on zeolite-catalysed methanol dehydration reactions and the effect on the catalytic dehydration of methanol in the presence of zeolite catalysts of various silica:alumina molar ratios (SAR).

The methanol dehydration reactions were carried out using the General Reaction Method and Apparatus described above in the presence of the catalysts and at the 5-nonanone concentrations specified in Table 1 below. The various promoter concentrations (relative to methanol) were achieved by adjusting the flow rate of 5-nonanone to be in the range 0.00013 mmol h$^{-1}$ to 0.013 mmol h$^{-1}$ depending on the desired promoter concentration to be achieved. The observed space time yields to dimethyl ether product are provided in Table 6.

TABLE 6

| Relative 5-nonanone concentration (mol %) | Dimethyl ether STY/g kg$^{-1}$ h$^{-1}$ | | | |
|---|---|---|---|---|
| | ZSM-5 SAR 23 | ZSM-5 SAR 80 | zeolite beta SAR 25 | zeolite beta SAR 150 |
| 0 | 852 | 429 | 218 | 113 |
| 0.001 | 1125 | 1019 | 981 | 1008 |
| 0.01 | 2287 | 3207 | 1929 | 1896 |
| 0.1 | 3433 | 4496 | 2336 | 2227 |

As can be seen from an inspection of Table 6, 5-nonanone can be used at a wide range of concentrations to provide an increase in space time yield to dimethyl ether in methanol dehydration reactions utilising zeolite catalysts of different silica:alumina molar ratios.

Examples 7 and 8

The diester compounds used in Examples 7 and 8 were obtained from Alfa Aesar or Acros Organics.

The zeolite used in Examples 7 and 8 was utilised in its H-form. The zeolite was obtained in ammonium-form from Zeolyst International and converted to H-form by calcination in air at 500° C.

The methanol dehydration reactions of Examples 7 and 8 were carried out utilising the General Reaction Method and Apparatus II described below.

General Reaction Method and Apparatus II

The methanol dehydration reactions were carried out using a 16-channel parallel fixed-bed stainless steel reactor system. Each reactor (10 mm internal diameter) housed a bed of catalyst mixed with silica dioxide diluent (0.168 g catalyst diluted with 0.337 g silica dioxide). The catalyst and silica dioxide each had a particle size of 450 to 900 microns diameter. The mixture was loaded on top of a 6.5 cm deep bed of an inert material (quartz sand). The reactor volume above the catalyst bed was also packed with quartz sand.

Each reactor was maintained at a temperature of 150° C. and at a total pressure of 1100 kPa throughout the reactions. A gaseous feed comprising 10 mol % methanol and inert gas was introduced into the reactor and allowed to flow through the catalyst bed for a period of 48 hours at which point a promoter compound was added to the feed to achieve a gaseous feed comprising 10 mol % methanol and 0.01 or 0.1 mol % promoter compound (relative to methanol). This gaseous feed comprising the promoter compound was introduced into the reactor for a period of 24 hours at a constant flow rate of methanol of 45 mmol h$^{-1}$ and a constant promoter flow rate of 0.0045 or 0.045 mmol h$^{-1}$.

The effluent stream from each reactor was cooled to 5° C. in a condenser and the gas phase from the condenser was periodically analysed by online gas chromatography to determine the yield of dimethyl ether product.

Example 7

This Example demonstrates the effect of various concentrations of cyclohexanone on dehydration reactions of methanol employing various catalysts.

The dehydration reactions were carried out using the General Reaction Method and Apparatus II described above and in the presence of the zeolite ZSM-5 with a silica:alumina molar ratio (SAR) of 20. The various promoter concentrations (relative to methanol) were achieved by adjusting the flow rate of cyclohexanone to be in the range 0.0045 mmol h$^{-1}$ to 0.045 mmol h$^{-1}$ depending on the desired promoter concentration to be achieved. The observed space time yields to dimethyl ether product are provided in Table

TABLE 7

| Relative cyclohexanone concentration (mol %) | Dimethyl ether STY/g kg$^{-1}$ h$^{-1}$ |
|---|---|
| 0 | 519 |
| 0.01 | 943 |
| 0.1 | 2192 |

As can be seen from an inspection of Table 6, cyclohexanone can be used at a range of concentrations to provide an increase in space time yield to dimethyl ether in methanol dehydration reactions.

Example 8

This Example demonstrates the effect of various concentrations of cyclopentanone on dehydration reactions of methanol employing various catalysts.

The dehydration reactions were carried out using the General Reaction Method and Apparatus II described above and in the presence of the zeolite ZSM-5 with a silica:alumina molar ratio (SAR) of 20. The various promoter concentrations (relative to methanol) were achieved by adjusting the flow rate of cyclopentanone to be in the range 0.0045 mmol h$^{-1}$ to 0.045 mmol h$^{-1}$ depending on the desired promoter concentration to be achieved. The observed space time yields to dimethyl ether product are provided in Table 8.

TABLE 8

| Relative cyclopentanone concentration (mol %) | Dimethyl ether STY/g kg$^{-1}$ h$^{-1}$ |
|---|---|
| 0 | 485 |
| 0.01 | 737 |
| 0.1 | 1462 |

As can be seen from an inspection of Table 8, cyclopentanaone can be used at a range of concentrations to provide an increase in space time yield to dimethyl ether in methanol dehydration reactions.

The invention claimed is:

1. A process comprising: dehydrating methanol to dimethyl ether product in the presence of a catalyst and a promoter, and in the absence of methyl acetate, wherein the catalyst is at least one solid Brønsted acid catalyst selected from aluminosilicate zeolites and heteropolyacids, and the promoter is at least one
   (i) a ketone of formula $R^1COR^2$ (Formula I)
      wherein $R^1$ and $R^2$ are identical or different and are each a $C_1$-$C_{11}$ alkyl group, or $R^1$ and $R^2$ together with the carbonyl carbon atom to which they are bonded form a cyclic ketone; or
   (ii) a ketal derivative of the ketone of Formula I; and
   wherein a molar ratio of the promoter to the methanol is maintained at 0.5 or less.

2. The process according to claim 1 wherein the ketone of Formula I is a straight alkyl chain ketone or branched alkyl chain ketone.

3. The process according to claim 1 wherein $R^1$ and $R^2$ are identical or different and each is a $C_1$-$C_3$ alkyl group.

4. The process according to claim 1 wherein $R^1$ and $R^2$ are different and $R^1$ is a $C_1$-$C_3$ alkyl group and $R^2$ is a $C_1$-$C_7$ alkyl group.

5. The process according to claim 1 wherein the ketone of Formula I is a cyclic ketone comprising 4 to 12 carbon atoms.

6. The process according to claim 1 wherein the ketal derivative of the ketone of Formula I is of formula

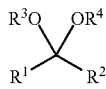

wherein $R^1$ and $R^2$ are identical or different and each is a $C_1$ to $C_7$ alkyl group, or $R^1$ and $R^2$ together with the carbonyl carbon atom to which they are bonded form a cyclic ketone; and each of $R^3$ and $R^4$ is an alkyl group or hydrogen with the proviso that $R^3$ and $R^4$ are not both hydrogen.

7. The process according to claim 1 wherein the ketal derivative of the ketone of Formula I is a dimethoxy ketal.

8. The process according to claim 1 wherein the molar ratio of the promoter to the methanol is maintained in a range 0.2:1 to 0.00001:1.

9. The process according to claim 1 wherein the promoter is added to the dehydration process.

10. The process according to claim 1 wherein the at least one solid promoter is generated in-situ in the dehydration process.

11. The process according to claim 1 wherein the Brønsted acid catalyst is a zeolite which zeolite is a hydrogen-form zeolite.

12. The process according to claim 1 wherein the at least one solid Brønsted acid catalyst is a zeolite which zeolite is a medium pore zeolite and is selected from framework types FER, MWW, MTT and TON.

13. The process according to claim 12 wherein in Formula I $R^1$ and $R^2$ are identical or different and each is a $C_1$-$C_2$ alkyl group.

14. The process according to claim 1 wherein the at least one solid Brønsted acid catalyst is a zeolite which zeolite is a large pore zeolite and is selected from framework types MFI, BEA and MOR.

15. The process according to claim 14 wherein in Formula I, $R^1$ and $R^2$ are identical and each is a $C_3$-$C_7$ alkyl group.

16. The process according to claim 1 wherein the process is carried out at a temperature of from 100° C. to 300° C.

17. The process according to claim 1 wherein the process is carried out as a heterogeneous vapour phase process.

* * * * *